United States Patent [19]

Rosencwaig

[11] Patent Number: 4,513,384
[45] Date of Patent: Apr. 23, 1985

[54] THIN FILM THICKNESS MEASUREMENTS AND DEPTH PROFILING UTILIZING A THERMAL WAVE DETECTION SYSTEM

[75] Inventor: Allan Rosencwaig, Danville, Calif.

[73] Assignee: Therma-Wave, Inc., Fremont, Calif.

[21] Appl. No.: 389,623

[22] Filed: Jun. 18, 1982

[51] Int. Cl.³ .................... G01N 25/00; G01N 29/04; G06F 15/00
[52] U.S. Cl. .................................... 364/563; 73/606; 73/643; 364/578; 374/4; 374/7; 374/134
[58] Field of Search ................ 374/7, 4, 134; 73/606, 73/602, 643; 367/7, 13; 364/578

[56] References Cited

U.S. PATENT DOCUMENTS

| | | | |
|---|---|---|---|
| 3,804,532 | 4/1974 | Patten et al. | 364/563 X |
| 3,978,713 | 9/1976 | Penny | 73/643 |
| 4,255,971 | 3/1981 | Rosencwaig | 73/606 |
| 4,271,705 | 6/1981 | Crostack | 73/602 |
| 4,274,288 | 6/1981 | Tittmann et al. | 73/602 X |
| 4,305,294 | 12/1981 | Vasile et al. | 73/602 X |
| 4,342,093 | 7/1982 | Miyoshi | 364/578 |
| 4,430,897 | 2/1984 | Quate | 73/606 |

OTHER PUBLICATIONS

Publ. "Photoacoustics & Photoacoustic Spectroscopy", pp. 270–284, vol. 57, Allan Rosencwaig, a Wiley–Interscience Publication, 1941, (1980 ©).
Publ. "Scanning Acoustic Microscopy", pp. 37–43, Weglein et al., 15th, A. P. Reliability Physics, Las Vegas, Nev., Apr. 12–14, 1977.
Publ. "Oblique Incidence Reflection Acoustic Imaging", Yeack et al., May 27, 1980 (J. Appl. Phys. 51(9), 9/1980), pp. 4637–4644.
"Thermal Wave Electron Microscopy of Metals", Allan Rosencwaig, Sep. 8, 1980, Thin Solid Films, 77 (1981), pp. L43-L47.

*Primary Examiner*—Daniel M. Yasich
*Attorney, Agent, or Firm*—Limbach, Limbach & Sutton

[57] ABSTRACT

The subject invention discloses a method for nondestructively determining the thickness of layers deposited on a substrate by analyzing thermal waves generated in a sample. The methods are particularly suited for use with integrated circuit manufacturing. In the subject method, the sample is subjected to a focused periodic heat source which generates thermal waves. Either the magnitude or phase of the thermal waves generated in the sample are measured. The values obtained are normalized relative to a reference sample. The normalized values are analyzed with respect to a theoretical model of the sample to calculate the thickness of the unknown layers. In an alternate embodiment, thermal characteristics can be determined in a sample as a function of depth. The latter approach is useful for nondestructively determining dopant concentrations or lattice defects in semiconductor devices as a function of depth beneath the surface.

12 Claims, 4 Drawing Figures

THIN FILM THICKNESS MEASUREMENTS AND DEPTH PROFILING UTILIZING A THERMAL WAVE DETECTION SYSTEM

The subject invention relates to a new and improved method for determining the thickness of a thin film layer on a substrate utilizing a thermal wave detection system. In addition, a method is disclosed for developing a depth profile of impurities, defects or some other depth-varying parameter in a sample. The subject methods are particularly suited for both detailed analysis and production procedures associated with the manufacture of integrated circuit devices.

BACKGROUND OF THE INVENTION

There is considerable interest in developing nondestructive techniques for evaluating subsurface conditions. This interest is particularly strong in the field of integrated circuit (IC) manufacturing. Typically, during the manufacture of an IC package, a wafer of silicon or other semiconductor material is covered with thin film layers. It would be desirable to provide a system which is capable of nondestructively measuring the thickness of the layers applied to the semiconductor substrate.

Another technique used in manufacturing semiconductor devices is the diffusion or implantation of ions or dopants into the lattice structure of the semiconductor. There is a need for a technique for nondestructively evaluating the concentration levels as a function of depth. A suitable depth profiling technique could also be used for quantifying lattice structure defects, such as vacancies or for measuring any other parameter that varies with depth in the material. As discussed below, the methods of the subject invention satisfy the above-stated needs utilizing a thermal wave detection system.

In a thermal wave microscope, thermal features beneath the sample surface are detected and imaged by sensing the thermal waves that scatter and reflect from these features. Thermal features are those regions of an otherwise homogeneous material that exhibit variations relative to their surroundings in thermal conductivity, thermal expansion coefficient or volume specific heat. Variations in these thermal parameters can arise from changes in basic material composition or from the presence of mechanical defects such cracks, voids and delaminations. Variations in thermal parameters can also arise from changes in the crystalline order or structure or due to the presence of small concentrations of foreign ions or lattice defects in an otherwise perfect crystal. It is believed that thermoacoustic microscopy was first disclosed in applicant's prior U.S. Pat. No. 4,255,971, issued Mar. 17, 1981, which is incorporated herein by reference. In thermoacoustic microscopy, thermal waves are generated by focusing an intensity modulated localized heat source at a microscopic point. As discussed in the above cited patent, there are a variety of techniques for applying the periodic heat source to the sample, for example, an intensity modulated beam of electromagnetic radiation or particle beams.

Irradiation of a sample with an intensity modulated beam of energy results in a periodic heating of the sample and in the generation of thermal waves. These thermal waves can be measured by a variety of techniques depending on which method of detection is chosen. One method of detection involves the measurement of the oscillating temperature of the surface of the sample at the spot of localized heating. The oscillating temperature can be measured by placing the sample in a photoacoustic cell and measuring the pressure oscillations in the cell induced by the periodic heat flow from the sample to the gas in the cell. (See, "Scanning Photo-Acoustic Microscopy", Y. H. Wong, Scanned Image Microscopy, Academic Press London, 1980.) The oscillating surface temperature may also be measured with a laser traversing the gas or liquid medium in contact with the heated spot on the sample surface. This laser beam will undergo periodic deflections because of the periodic heat flow from the sample to the adjacent medium. (See, "The Mirage Effect in Photothermal Imaging", Fournier and Boccara, Scanned Image Microscopy, Academic Press London, 1980.) A third technique for measuring the oscillating surface temperature utilizes an infrared detector that measures the periodic infrared emission from the heated spot on the surface of the sample. (See, "Photothermal Radiometry for Spatial Mapping of Spectral and Material Properties", Nordal and Kanstad, Scanned Image Microscopy, Academic Press London, 1980.)

Another method for detecting thermal waves involves the measurement of the thermal displacement of the sample surface at the spot of localized heating. Techniques for carrying out the latter method include the use of a laser probe or a laser interferometer. (See, "Photo Displacement Imaging", Ameri, et al., Photoacoustic Spectroscopy Meeting, Technical Digest, Paper THA6-2, Optical Society of America, 1981).

A third methodology for detecting the thermal waves involves the measurement of acoustic signals. Acoustic waves are generated by the thermal waves in the sample because thermally induced stress-strain oscillations are set up in the heated region of the sample. These acoustic waves can be detected by a variety of techniques including a laser probe (See, "Probing Acoustic Surface Perturbations by Coherent Light", Whitman and Korpel, Applied Optics, Vol. 8, pp. 1567-1580, 1969); a laser interferometer (See, "Measurements Using Laser Probes", De La Rue, et al., Proc. IEE, Vol. 119, pp. 117-125, 1972); or with an acoustic transducer, such as a piezoelectric transducer, in acoustic contact with the sample. (See, U.S. pat. No. 4,255,971, cited above). Any of the above-described methods can be used to detect and measure thermal waves for performing thermal wave imaging and microscopy.

In addition to imaging, thermoacoustic microscopy can be used for other types of analyses. For example, thermoacoustic microscopy can be used to analyze the plate-mode resonant signature of bonded members to determine the quality of the bond therebetween. The latter technique is disclosed in applicant's copending U.S. patent application, Ser. No. 381,891, filed May 25, 1981, and now U.S. Pat. No. 4,484,820, which is incorporated herein by reference. As disclosed in the subject application, thermal wave detection can also be used for determining the thickness of a thin film layer on a substrate and for obtaining a profile of the concentration of thermal characteristics in a sample as a function of depth.

Accordingly, it is an object of the subject invention to provide a new and improved method for determining the thickness of a thin film applied to a substrate.

It is another object of the subject invention to provide a new and improved method for determining the thickness profile of a multilayer thin film structure utilizing thermal wave techniques.

It is a further object of the subject invention to provide a new and improved method for determining the thickness of the topmost layer in a multilayer structure using a thermal wave technique.

It is still another object of the subject invention to provide a method for profiling as a function of depth, a sample that has had its lattice structure locally disrupted through the diffusion or implantation of foreign ions, such as dopants.

It is still a further object of the subject invention to provide a method for profiling, as a function of depth, a sample containing imperfections in its lattice structure.

It is still another object of the subject invention to provide a method for evaluating a sample having thermal characteristics that vary as function of depth for any reason.

It is still a further object of the subject invention to provide a new and improved method for evaluating the thickness of a layer of material on a substrate wherein a thermal wave signal of the sample is compared with an expected thermal wave signal associated with a reference sample.

SUMMARY OF THE INVENTION

In accordance with these and many other objects, the subject invention provides for new and improved methods for nondestructively analyzing the structure of a sample. In order to interpret the results of thermal wave detection on a sample, it is necessary to construct a mathematical model that provides expressions for the temperature at and beneath the surface of the sample and for the thermoelastic response beneath its surface. If thermoacoustic detection is used, the model must also take into effect the elastic wave propagation and interference effects in the sample. The model must also include all of the experimental parameters, such as the character of the incoming heat source, the character of the sample, and the type of detector used. These parameters must be considered since they affect the detected thermal wave signals. For example, the magnitude and phase of thermal waves generated in material are a function of the power and modulation frequency of the beam. In addition, the thermal waves are also a function of the sample's density, specific heat and thermal conductivity. The type of detection system used also effects the thermal wave signals. Thus, it is very important to consider thermal expansion coefficients and the elastic coefficient of the sample when thermal displacement and thermoacoustic detection is utilized.

One proposal for developing a model for profiling thermal characteristics in a sample, as a function of depth, utilizing a photoacoustic technique, is disclosed in applicant's book "Photoacoustics and Photoacoustic Spectroscopy", A. Rosencwaig, Wiley Interscience, New York 1980. In order to analyze the signals detected as a result of thermal waves, a new mathematical model must be developed. Attached to this application as Appendix A, applicant presents the derivation of a mathematical model of a one-dimensional multilayer system which can be utilized to carry out the calculations proposed in the subject invention. While it is believed that the mathematical approach disclosed in the appended article represents a fairly accurate characterization of the interactions within a sample, it is to be understood that the scope of the subject invention is not to be limited by the exemplary model. In contrast, in the future it is expected that more sophisticated two and three-dimensional models may be developed which could add to the accuracy of the determinations.

The proposed model provides a basis for calculating expected values of thermal wave signals based on all the parameters in a given experiment, such as beam power, the type of detection system used and the sample's characteristics. As discussed below, by analyzing the experimental data obtained in accordance with the subject method, with respect to the model, significant information can be developed concerning the subsurface characteristics of the sample.

In accordance with one method of the subject invention, the thickness of a thin film layer deposited on a substrate is determined. In this method, a periodic heat source is focused on the uppermost layer deposited on the substrate. The thermal waves generated are then detected and the value of either their magnitude or phase is recorded.

This value is normalized against a measurement taken of a reference sample. The reference sample consists of a substrate of known construction. The normalized values are then compared to values derived from a mathematical model corresponding to the experimental parameters. In the preferred embodiment, the comparison is accomplished using a least-squares fitting routine whereby a determination of the thickness of the thin film layer can be made.

The above described technique can be applied to profile the thicknesses of a multilayer deposition on a substrate. As disclosed in the Appendix, the multilayer model is expanded recursively to obtain a mathematical expression accounting for a plurality of layers having different characteristics. Since each layer presents another unknown, to solve the equation it is required to provide additional experimental data points. Accordingly, for multilayer determinations, measurements of the thermal wave signals are taken at a plurality of modulation frequencies of the heating source. At a minimum, the number of test frequencies used must exceed the number of unknown layers to be determined.

In another embodiment of the subject invention, a method for generating a depth profile of the concentration of dopants, impurities or defects in a sample is disclosed. The subject method may be used, for example, to determine the concentration, as a function of depth, of dopants infused into a structure. In the latter method a variation of the multilayer mathematical model can be used. More particularly, in the mathematical analysis, a portion of the upper surface of the sample is divided into hypothetical layers of fixed depth. The unknowns in the equations becomes the thermal conductivity of each layer. In the subject method, thermal waves are detected at a plurality of modulation frequencies. The number of frequencies detected must exceed the hypothetical number of layers to be analyzed. The normalized values are then compared with expected values derived from the model. By this arrangement, the thermal conductivity characteristics of the sample can be plotted as a function of depth. By relating the thermal conductivity characteristics to known effects of impurity levels, the concentration of the dopants can be determined.

In another aspect of the subject invention, a method is disclosed wherein the thickness of a layer on a substrate can be evaluated. More particularly, in a production situation, it will be possible to determine the expected thermal wave signal associated with a desired thickness. Accordingly, by taking proper thermal wave measurements, a comparison can be made to predetermined values, representative of the desired sample, for evaluating the thickness of the layer.

Further objects and advantages of the subject invention will become apparent from the following detailed description taken in conjunction with the drawings in which:

DETAILED DESCRIPTION OF THE PREFERRED EMBODIMENTS

Figure 1:
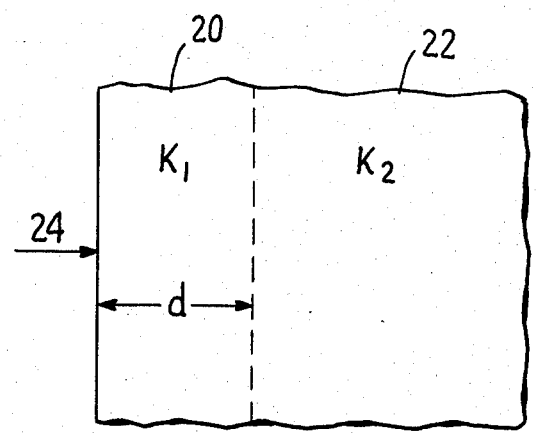
FIG. 1 is a graphic representation of a two-layer model for a thin film on a thick substrate.

In order to analyze the thermal wave signals detected when a sample is tested, a mathematical model must be developed. Referring to FIG. 1, a two-layer representation for a thin film layer 20 deposited on a thick substrate 22 is illustrated. Using such a representation, mathematical expressions can be derived for explaining the effects of thermal waves.

As discussed above and in the previously cited references, thermal waves can be detected by measuring variations in temperature or thermal displacement at the surface or by detecting the thermoacoustic signal generated by the thermal waves. In any case, the detected signal will be periodic in response to the amplitude modulated incoming heat source. These signals are quantified by correlating either the magnitude of the output signal or its phase in relation to the incoming modulation signal.

The output signal detected will depend on a variety of parameters, including the frequency of the modulation signal the method of detection and the type of material being tested. Because there are so many factors effecting measurement, an absolute standard cannot be conveniently used. Accordingly, measurements of the thermal waves must be normalized against a reference sample. As discussed below, the reference sample is defined based upon the type of information which is being sought.

Figure 2:
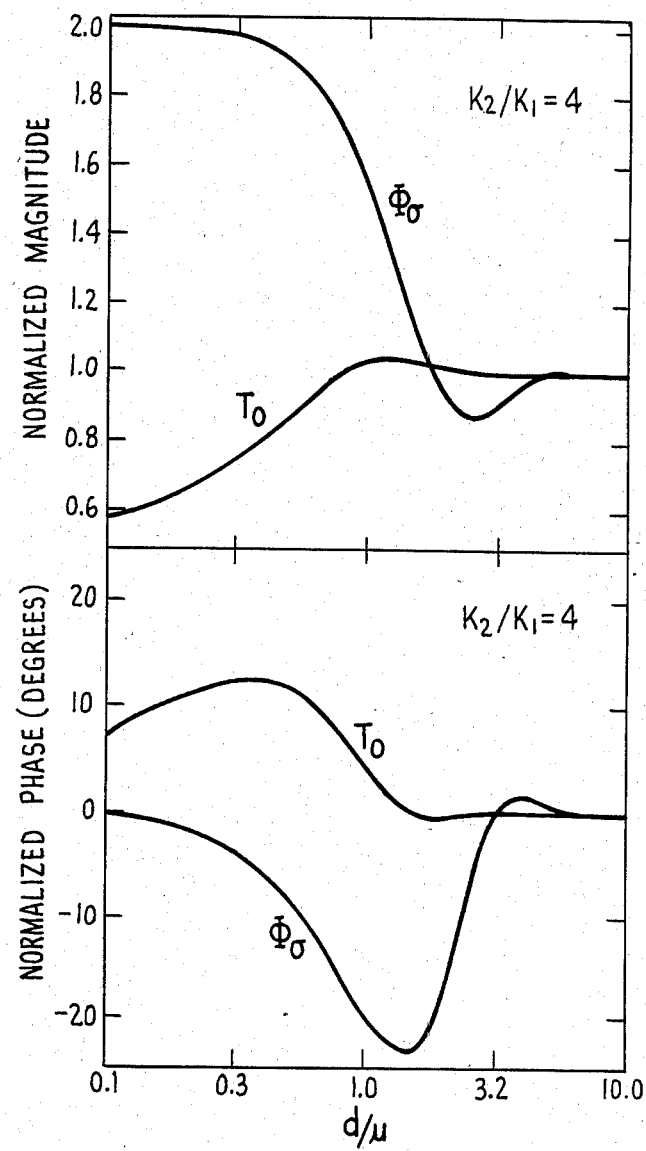
FIG. 2 is a graph showing the relationship between the phase and magnitude of thermal wave signals as a function of depth and frequency.

As discussed above, the normalized values of either the phase or magnitude of the thermal wave signals are used to determine the desired information. This result is possible because the magnitude and phase of the thermal wave signal varies with the modulation frequency for a particular ratio of two thermal conditions. The graphs displayed in FIG. 2 plot normalized values for the magnitude and phase parameters, in a two layer model illustrated in FIG. 1 where the thermal conductivities K are related as $K_2/K_1 = 4$. In the graphs, the X axis is frequency normalized in units of $d/\mu$ where d is the thickness of the top layer and $\mu$ is the thermal diffusion length given by $$\mu = \left(\frac{2K}{\rho C \omega}\right)^{\frac{1}{2}}$$

where $\rho$ is the density, C is the specific heat and $\omega$ is the beam modulation frequency in radians per second. The curves illustrate how the normalized parameters of magnitude and phase vary over both the depth of the layer and frequency of the modulation beam.

Turning now to the method of the subject invention, a value for either the phase or magnitude of the thermal waves, needed to achieve normalization, is obtained by focusing a periodic heat source on a reference sample. In the situation where the thickness of a single layer deposited on a substrate is to be determined, the reference sample can be the uncoated substrate. Since the phase and magnitude of the detected signals are not dependent upon the thickness of a uniform reference sample, any sample corresponding to the substrate to be tested may be used as a reference sample.

A periodic heat source 24 is then impinged on the upper surface of thin layer 20. As discussed in the Appendix, the thermal wave generated will be scattered and reflected from the boundary between the thin layer 20 and the substrate 22. This effect can be observed by noting the variation either in the magnitude or the phase of the thermal waves detected.

The magnitude or phase values measured are then normalized, to derive a value which is representative of the layer to be analyzed. As is well-known, magnitude values can be normalized by calculating the ratio between the reference value and the sample value. Since phase measurements are periodic, the normalization of these values can be obtained by subtracting the reference phase from the test sample phase. A measurement of either the magnitude or the phase can be used in the method of the subject invention. In many cases, the measurement of normalized phase will be preferred since phase measurements are dependent on fewer experimental variables than are the magnitude measurements.

Once the parameter values have been normalized, they are compared with expected normalized values derived from the model which is being utilized. One suitable model is disclosed in the Appendix attached hereto. The mathematical model takes into account all experimental parameters, and is arranged in an expression which varies as a function of depth.

In order to obtain an unambiguous determination of the thickness "d" of layer 20, it is preferable to make measurements on the sample at a plurality of beam modulation frequencies. Thereafter, the experimental data obtained is applied to a mathematical equation defining the model and the equation is solved for "d". Preferably, the equation is solved using well-known least-squares fitting routines which optimize the fit between the experimental results and the theoretical model. The accuracy of the results will be enhanced by providing additional experimental data points derived by obtaining a plurality of information at various beam modulation frequencies.

Figure 4:
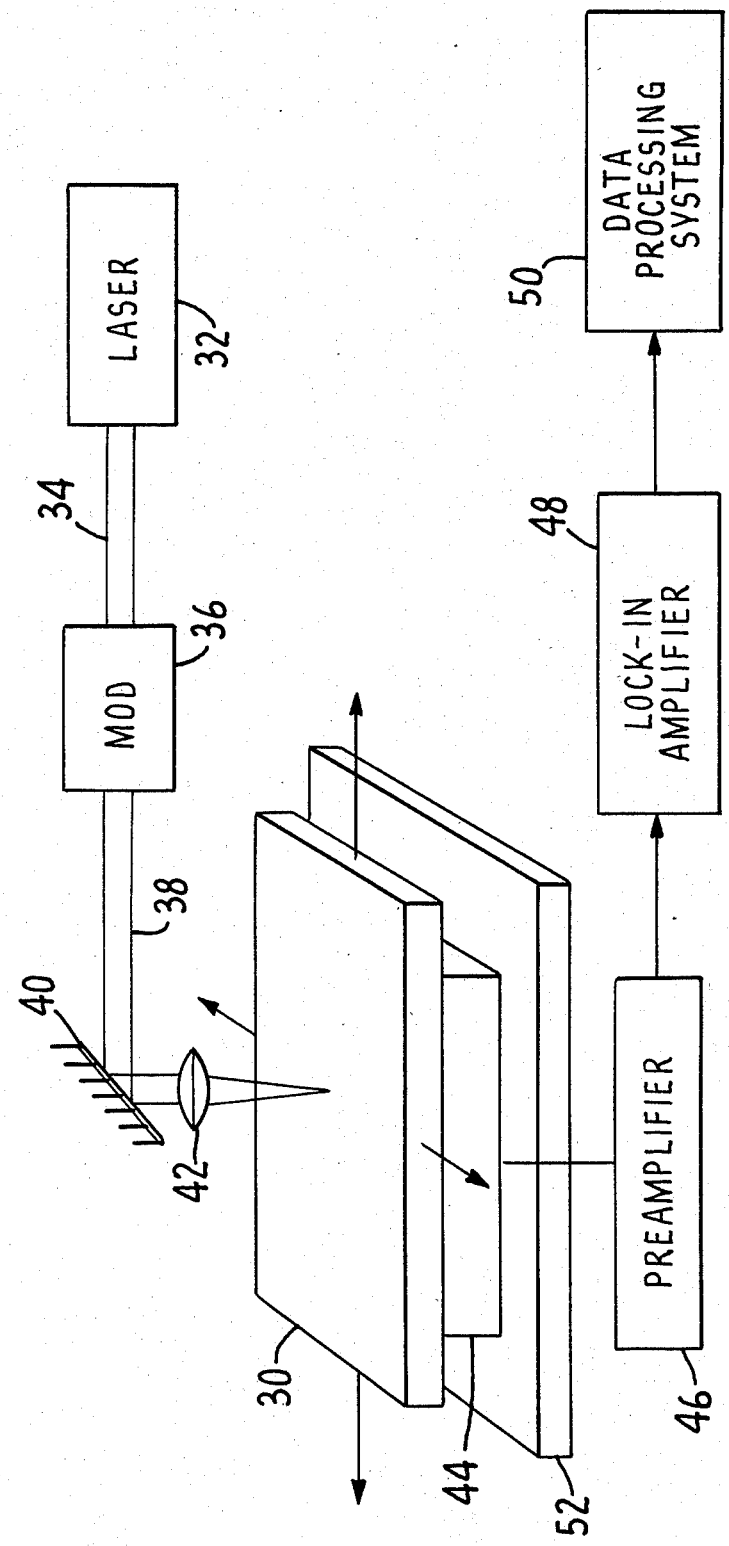
FIG. 4 is a schematic diagram illustrating a representative arrangement for carrying out the steps of the method of the subject invention.

Referring to FIG. 4, a schematic illustration of a device suitable for performing the steps of the subject method is illustrated. The device is described in detail in applicant's prior U.S. Pat. No. 4,255,971, previously incorporated herein by reference.

In FIG. 4, a sample 30 is shown being subjected to a modulated heat source for exciting thermal waves in the sample. As set forth above, a variety of means may be provided for exciting the thermal waves. In the illustrated embodiment, the means is defined by a CW laser 32 which emits an optical beam 34 that is modulated by modulator 36. The intensity modulated output 38 of modulator 36 is deflected by a mirror 40 through a microscope objective 42 and onto the surface of the sample.

The thermal waves generated by the modulated output 38 can be detected in a variety of ways. In the illustrated embodiment, the sample is placed in contact with a piezoelectric transducer 44, the output of which is supplied to a preamplifier 46. The output of the preamplifier 46 is fed to a lock-in amplifier 48 that is tuned to the modulation frequency of the heating beam. Finally, the output of the lock-in amplifier is supplied to a data processing system 50 capable of measuring the parameters discussed above. Data processing system 50 is also capable of normalizing and comparing the measured signals to derive the mathematical models referred to above.

FIG. 4 also illustrates a movable stage 52 controlled by data processing system 50 for rastering the sample with respect to the heating beam. It should be understood that the means depicted for providing the periodic heating and for measuring the thermal waves are intended only to be illustrative and in no way limiting on the scope of the subject invention.

The above described technique provides for a method for yielding a quantitative measurement of the thickness of an uppermost layer deposited on a substrate. In some manufacturing situations, it is not necessary to calculate the actual thickness of the layer deposited but rather to determine if that thickness corresponds to a desired thickness. Stated differently, in a manufacturing setting, it may be necessary to determine only if the thickness of a particular coating corresponds to the desired thickness and is therefore satisfactory, rather than having to calculate the actual thickness of the coating.

In the latter situation, it may be unnecessary to compare the data measured during testing with theoretical data derived from a normalized model. Rather, the experimental results can be compared to a predetermined expected result, corresponding to a sample having a layer deposited with the desired thickness. Thus, the subject invention contemplates a method wherein the experimentally derived normalized parameter is compared to a predetermined normalized parameter for evaluating whether the thickness of the layer in question corresponds to the predetermined thickness layer. As with the first described method, in order to eliminate any ambiguity, it would be desirable to take a plurality of measurements at various modulation frequencies.

The latter method may be particularly suited for integrated circuit manufacturing technique wherein layers of material are deposited on a silicon or other semiconductive substrate. After arriving at a predetermined value corresponding to a satisfactory construction, each manufactured IC can be scanned and measured. If the measured values correspond to the predetermined values, the coating thickness can be classified as satisfactory.

Figure 3:
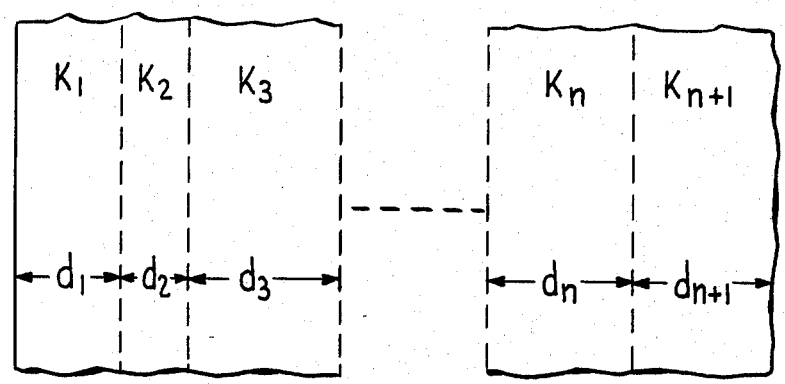
FIG. 3 is a graphic representation of a model for a multilayer system.

In order to obtain a thickness profile of a multilayer thin film structure, a multilayer model must be developed. More particularly, and referring to FIG. 3, the number of layers in the model must be equal to the number of layers in the structure to be evaluated. Using a reiterative version of the two-layer model discussed above, an expression representing the thicknesses of the various layers can be calculated.

In this analysis, the thermal parameters ($K_1$-$K_n$) of each layer is known. In order to calculate all of the unknown thicknesses ($d_1$-$d_n$), it is necessary to experimentally provide a number of data points which exceeds the number of unknown thicknesses. Accordingly, in the method of the subject invention, the values of parameters are determined at a plurality of selected modulation frequencies wherein the number of modulation frequencies selected is greater than the number of unknown layers. In this situation, wherein the thickness of a plurality of layers is to be determined, the normalization of the values obtained will be relative to the underlying uncoated substrate. As in the previous example, this reference sample can be either the actual sample prior to deposition of the layers or another sample having a similar structure and thermal characteristics.

The depth of penetration of the thermal waves for effective imaging is dependent upon their wavelength. More particularly, longer wavelengths, and hence lower modulation frequencies will provide images to a greater depth. Thus, in multilayer analyses, the frequencies selected must include wavelengths sufficient to provide information as to the lowest layer of interest.

In order to determine the thickness of only the topmost layer, in a multilayer structure, where all the other layer thicknesses are known, multiple measurements, as required in the previously described method are not required. More particularly, when the other thickness layers are known, their valves can be applied to the theoretical multilayer model with only the thickness of the uppermost layer being an unknown. In this instance, the reference sample used for normalization will be the multilayer structure prior to the topmost layer being deposited. By this arrangement, the experimental values derived will respresent only that of the uppermost layer. As in the determination of a single layer thickness, measurements at additional modulation frequencies will reduce the likelihood of ambiguities in measurement.

By using the multilayer model in a different approach, it is possible to profile a sample's thermal characteristics as a function of depth. This technique is of extreme interest in the field of integrated circuit manufacture where it is desirable to examine the lattice structure of semiconductor materials, such as silicon. More particularly, manufacturers frequently diffuse or implant ions or dopant materials in the silicon structure in order to effect its semiconductive properties. The subject method can be utilized to develop a profile of the concentration of these dopants as a function of depth from the surface of the material. Another use for the subject method would be to analyze defects, such as dislocations or vacancies, in the lattice structure as a function of depth.

As can be appreciated, in the above discussed multilayer model, determination of layer thicknesses was made based upon prior knowledge of the thermal characteristics of each material layer deposited. Thus, while the thicknesses were unknown, all other thermal characteristics were known. In this embodiment of the subject method, the sample is treated as a multilayer structure having unknown thermal characteristics. Further, the model is divided into a plurality of hypothetical layers of a known thickness. Thus, the unknowns in the mathematical model become thermal characteristics such as the thermal conductivity, while the thickness of the layers are known. As discussed below, by calculating the thermal characteristics as a function of depth, a depth profile of dopant concentrations can be derived.

In accordance with the subject method, a periodic heat source is focused on the nonuniform sample. Measurements of one of either the magnitude or phase parameters of the thermal wave signal are taken at selected modulation frequencies. Similar to the multilayer method, the number of frequencies used must exceed the number of hypothetical layers being investigated. As can be appreciated, resolution of the depth profile can be increased by increasing the number of hypothetical layers. However, since an increase in the number of hypothetical layers requires an increased number of test frequencies, the length of time for an examination will increase. Thus, in a manufacturing situation, the need to maximize the resolution of the depth profile can be balanced against the time necessary to carry out the measurements.

As in the previous methods, the values obtained must be normalized against a reference sample. In the instant method, the reference sample is characterized by a uniform or nontreated material. By this arrangement, the effects of the dopant or lattice irregularities can be directly analyzed.

Similar to the calculations described for the multilayered determination, the measured data is analyzed with a least-squares fitting routine relative to the multilayer model. As pointed out above, in this analysis, the thicknesses of the layers are known, while the thermal characteristics of the layers are unknown. Once the thermal conducitivites of the layers are calculated, it is necessary to obtain a correlation between the thermal conductivity of the lattice with respect to the concentration of dopants or defects in the lattice. Stated differently, a relationship must be established between the value of the thermal conductivity and the level of dopants or defects in the lattice. Such a correlation may be obtained from calibration experiments or from direct measurements of thermal conductivity for different concentrations of dopants or defects.

Thus, by this method, values can be derived which represent the concentration levels of dopants or impurities in each hypothetical layer. This information provides a profile, as a function of depth of the desired characteristic.

In summary, there has been disclosed new and improved methods for determining the thickness of a layer of material deposited on a substrate by studying the phase or magnitude parameter of the detected thermal wave signals. In the subject method, a periodic heat source is focused on the sample. A measurement is made of one of the parameters of the thermal wave signal. The measurements are taken at a plurality of beam modulation frequencies, with the number of frequencies selected being greater than the number of layers whose thicknesses are to be determined. The values are normalized relative to the values obtained from a reference sample. The normalized values are then analyzed with respect to a mathematical model of the multilayer system. The model represents a set of equations taking into account all phenomena associated with the thermal wave generation within the sample. Using a least square fitting routine, the unknown thickness of each layer can be calculated. In an alternate method of the subject invention, a profile of the thermal characteristics of a sample caused, for example, by dopants or lattice defects can be determined as a function of depth. In the latter case, the theoretical model is divided into a number of hypothetical layers of known thickness. Using a least-squares fitting routine on data obtained at various modulation frequencies, the thermal characteristics, and in particular the thermal conductivity of the hypothetical layers can be determined. The thermal conductivities can be related to the concentration of dopants or lattice defects to provide an accurate depth profile of the sample.

While the subject invention has been described with reference to preferred embodiments, it is to be understood that various other changes and modifications could be made therein by one skilled in the art without varying from the scope and spirit of the subject invention as defined by the appended claims.

I claim:

1. A method for determining the thickness of at least one layer of material deposited on a substrate by measuring the value of either the phase or magnitude parameters of thermal wave signals generated by a focused periodic heat source comprising the steps of:
   deriving a model that provides expressions for the temperature at and beneath the surface of a known reference sample and for the thermoelastic response beneath the surface of the known reference sample;
   focusing said periodic heat source on the uppermost layer deposited on said substrate;
   measuring the value of one of said parameters of the thermal wave signals at a plurality of selected modulation frequencies of said heat source wherein the number of modulation frequencies selected is greater than the number of layers whose thickness is to be determined;
   normalizing the measured value of said parameter of each modulation frequency selected relative to the value of said parameter determined for said known reference sample; and
   comparing said normalized values to expected normalized values derived from said model depicting the thermal process in said reference sample whereby the thickness of each said layer can be determined.

2. A method as recited in claim 1 wherein the thermal wave signals are measured with a means which detects the acoustic signals that are generated by the thermal waves.

3. A method as recited in claim 2 wherein said detection means includes an ultrasonic transducer.

4. A method as recited in claim 1 wherein the parameter measured is the phase of the thermal wave signals and the values are normalized by subtracting the value of the phase of the reference sample from the phase of the multilayer substrate.

5. A method as recited in claim 1 wherein the parameter measured is the magnitude of the thermal wave signals and wherein said normalized values are defined as the ratio between the value obtained from the reference sample and the value obtained from the multilayer substrate.

6. A method for determining the change in thermal characteristics as a function of depth in a nonuniform sample having impurities or defects therein by measuring the value of either the phase or magnitude parameter of thermal wave signals generated in said sample by a focused periodic heat source comprising the steps of:
   deriving a model that provides expressions for the temperature at and beneath the surface of a known reference sample and for the thermoelastic response beneath the surface of the known reference sample, with said model being characterized as having a plurality of layers of known thickness;

focusing said periodic heat source on said nonuniform sample;

measuring the value of one of said parameters of said thermal wave signals generated in said nonuniform sample at a plurality of selected modulation frequencies with the number of selected modulation frequencies being greater than the number of layers defined in said model;

normalizing the measured value of said one parameter at each modulation frequency relative to the value of said one parameter determined for said known reference sample; and comparing said normalized values to expected normalized values derived from said model whereby the thermal characteristics of the layers in said model can be determined and therefore the depth variation of these thermal characteristics in the nonuniform sample can be evaluated.

7. A method as recited in claim 6 wherein the thermal characteristics are the thermal conductivities of the hypothetical layers and further including the step of correlating the concentration of impurities or defects in the sample to variations in the thermal conductivity such that a profile of the impurities or defects can be obtained as a function of depth.

8. A method as recited in claim 6 wherein the measurements of said one parameter is taken at a plurality of modulation frequencies whereby the resolution of said depth variations is increased.

9. A method as recited in claim 6 wherein the thermal wave signals are measured with a means which detects the acoustic signals that are generated by the thermal waves.

10. A method as recited in claim 9 wherein said detection means includes an ultrasonic transducer.

11. A method as recited in claim 6 wherein the parameter measured is the phase of the thermal wave signals and the values are normalized by subtracting the value of the phase of the reference sample from the phase of the non-uniform sample.

12. A method as recited in claim 6 wherein the parameter measured is the magnitude of the thermal wave signals and wherein said normalized values are defined as the ratio between the value obtained from the reference sample and the value obtained from the nonuniform sample.

* * * * *